United States Patent [19]
Pierce

[11] Patent Number: 5,405,359
[45] Date of Patent: Apr. 11, 1995

[54] TOGGLE WEDGE

[76] Inventor: Javi Pierce, 4780 Mountain Rd., Stowe, Vt. 05672

[21] Appl. No.: 235,345

[22] Filed: Apr. 29, 1994

[51] Int. Cl.⁶ .................................. A61B 17/04
[52] U.S. Cl. ........................... 606/232; 606/72
[58] Field of Search ............... 606/72, 74, 75, 76, 606/77, 86, 220, 72–86; 411/456, 508, 509, 913

[56] References Cited

U.S. PATENT DOCUMENTS

| | | | |
|---|---|---|---|
| 4,716,893 | 1/1988 | Fisher et al. | 606/72 |
| 4,870,957 | 10/1989 | Goble et al. | 606/232 |
| 4,898,156 | 2/1990 | Gatturna et al. | 606/232 |
| 5,037,422 | 8/1991 | Hayhust et al. | 606/232 |
| 5,102,421 | 4/1992 | Anspack, Jr. | 606/232 |
| 5,141,520 | 8/1992 | Goble et al. | 606/232 |
| 5,176,682 | 8/1992 | Chow | 606/232 |
| 5,324,308 | 6/1994 | Pierce | 606/232 |

Primary Examiner—Gary Jackson
Attorney, Agent, or Firm—John J. Welch, Jr.

[57] ABSTRACT

A toggle wedge is hereof depicted that serves as a suture anchor in bone or soft tissue to which further soft tissue can be sutured in close opposition thereto which wedge is made up of a top portion characterized by the presence of a barbed tip, three smooth sides, one side with two paired suture entry holes in its upper portion, a centrally located suture exit hole at the bottom of this upper portion, an outwardly inclined stop face separating this side's upper portion and this sides lower portion, a tooth centered on the bottom portion of a rounded notch cut into the lower part of this lower portion and a base containing a centrally located suture entry hole and two paired suture exit holes found in an inclined portion of the base.

6 Claims, 8 Drawing Sheets

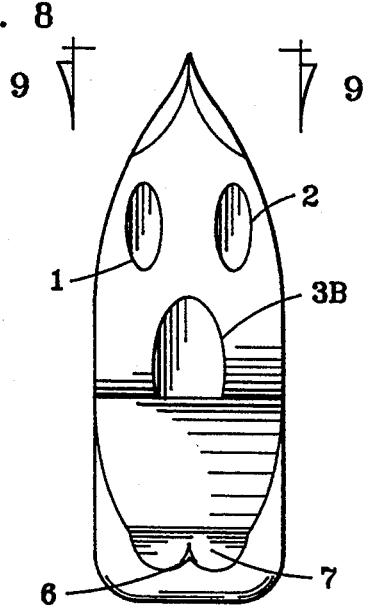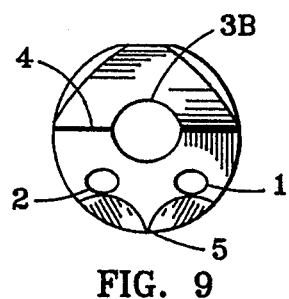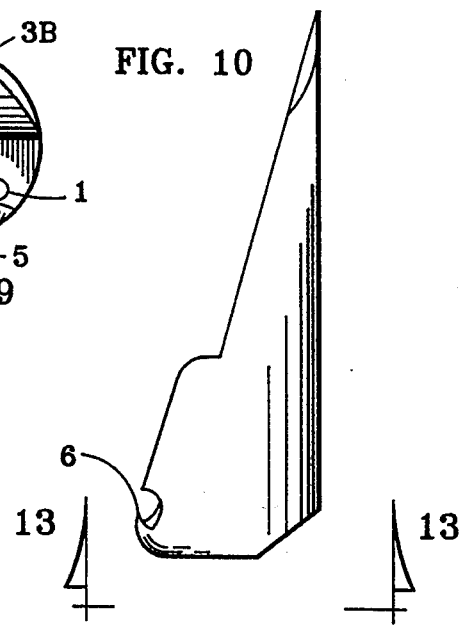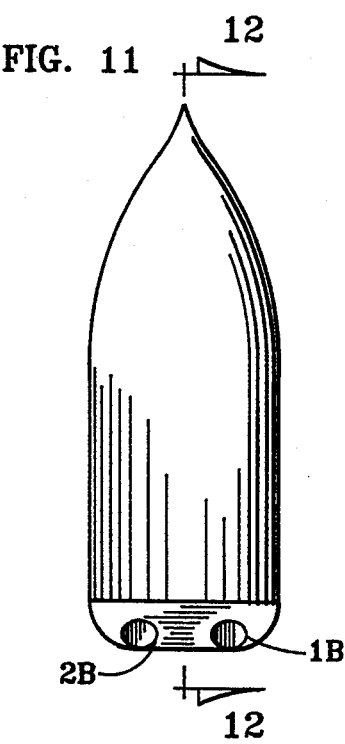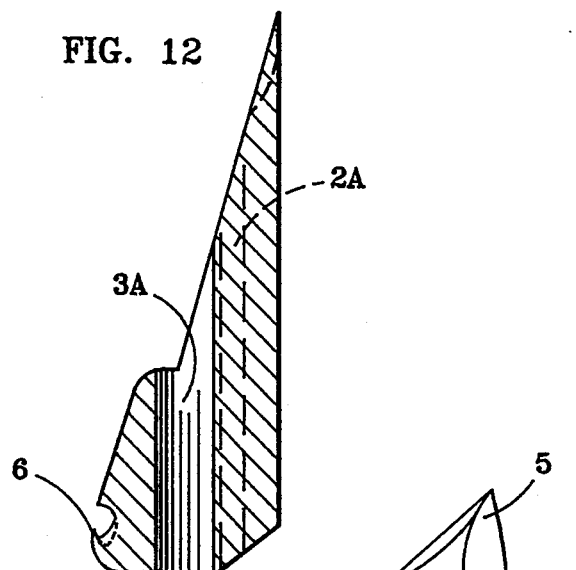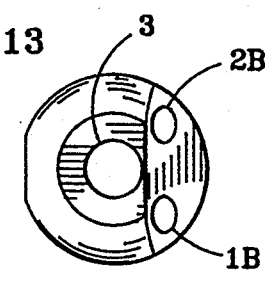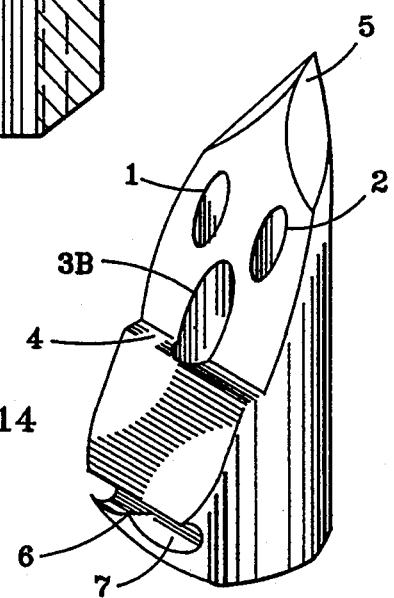

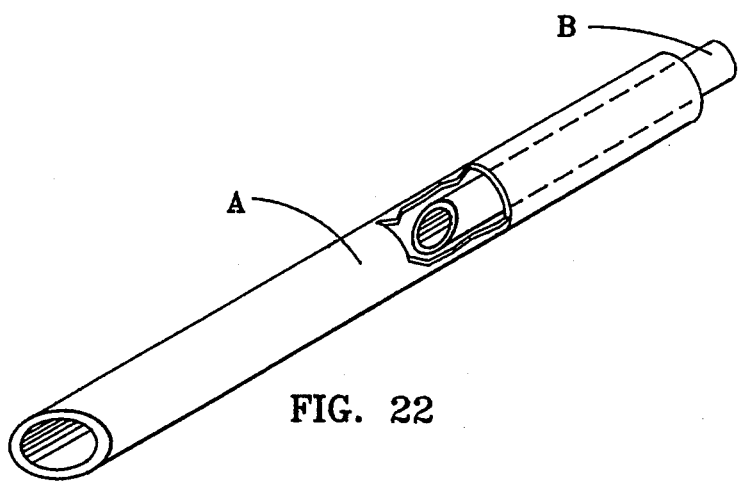
FIG. 22
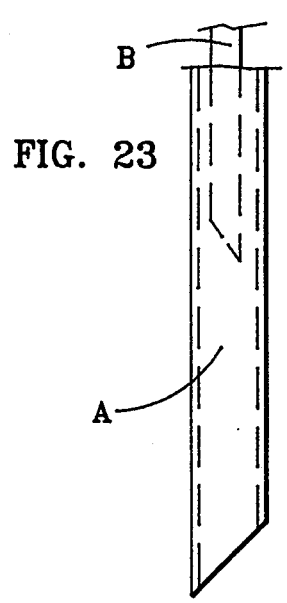
FIG. 23
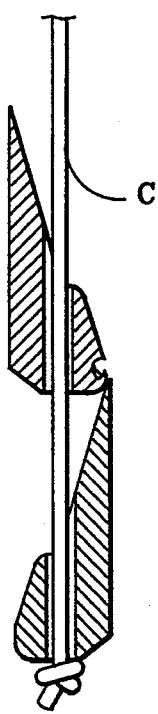
FIG. 24
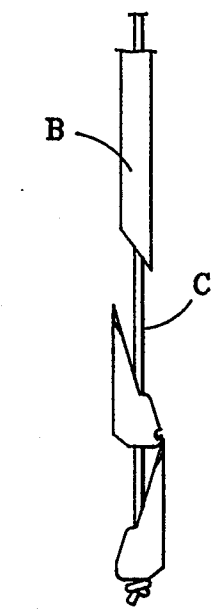
FIG. 25
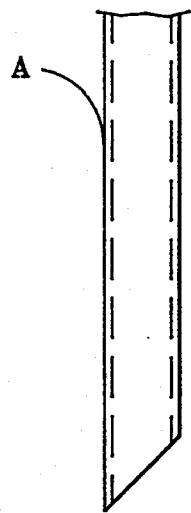
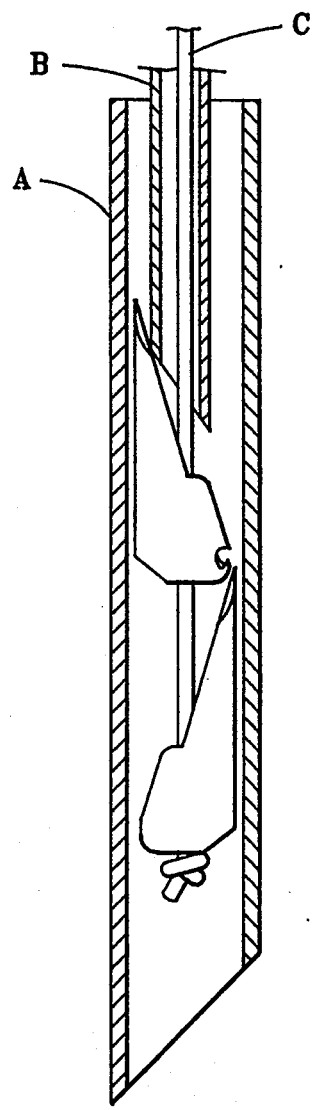
FIG. 26

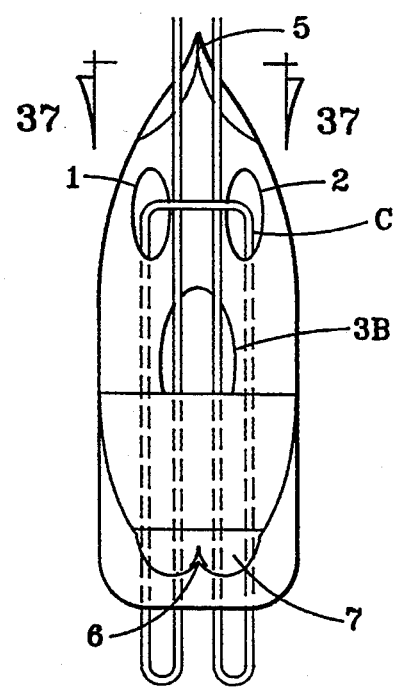
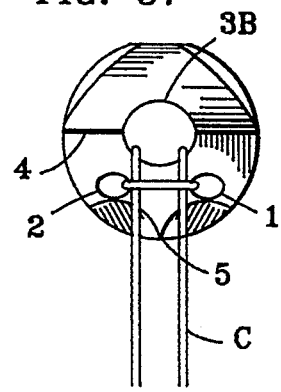
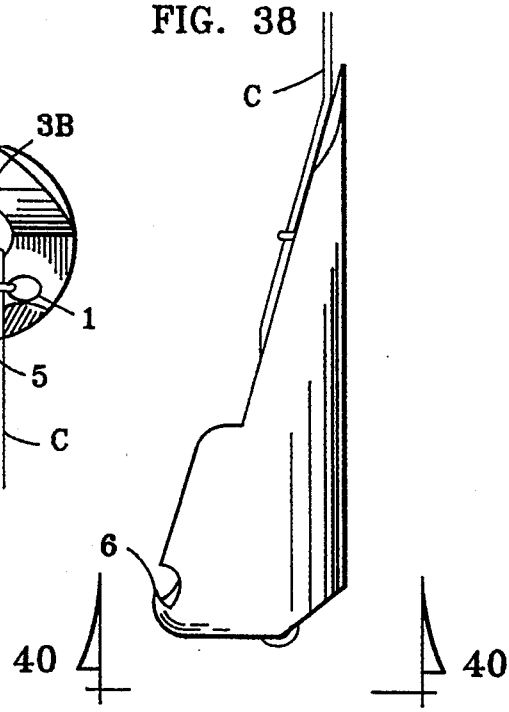
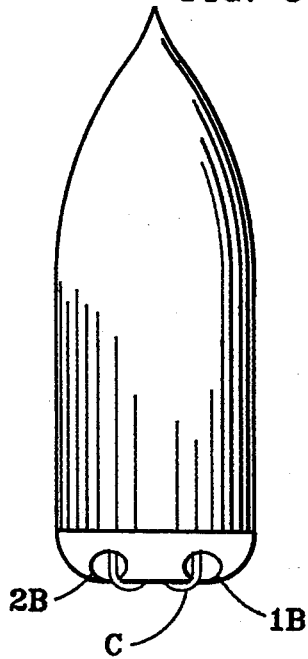
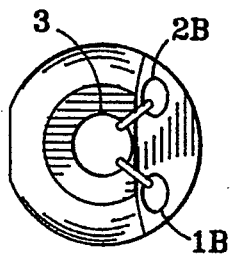
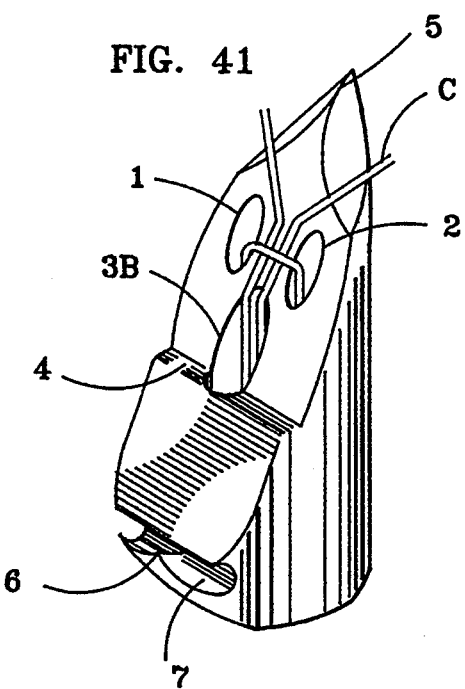

TOGGLE WEDGE

CROSS REFERENCES TO PRIOR APPLICATIONS

There are no prior or applications related to this application. The instant invention is related to the patent issued on the 28th day of June, 1994 to applicant, Javin Pierce, namely U.S. Pat. No. 5,324,308 entitled, "Suture Anchor".

FEDERALLY SPONSORED RESEARCH AND DEVELOPMENT

There is no involvement with federally sponsored research and development.

BACKGROUND OF THE INVENTION

1. Field of the Invention

The instant invention relates to that panoply of devices that serve to anchor to bone or soft tissue, suture materials for the purpose of facilitating adherence of soft tissues such as muscle and ligament tissues in close apposition to such bone or soft tissue by way of such suture materials being sewn thereto and therein.

2. Possible Prior Art

The following patents may bear somewhat on the essence of the instant invention. However, the instant invention represents a manifest improvement upon and variation from any other arguably similar devices current in or out of vogue within the scope of the field of such devices.

| Inventor | Invention | Patent No. | Date |
|---|---|---|---|
| 1. Goble et al | Harpoon Suture Anchor | 5,141,520 | 8/25/92 |
| 2. Gatturna et al | Suture Anchor | 4,898,156 | 2/6/90 |
| 3. Chow | Surgical Implement | 5,176,682 | 1/5/93 |
| 4. Anspack, Jr. | Surgical Anchoring and Method of Forming | 5,102,421 | 4/7/92 |
| 5. Fischer et al | Bone Fastener | 4,716,893 | 1/5/88 |
| 6. Goble et al | Ligament Anchor System | 4,870,957 | 10/3/89 |
| 7. Hayhurst et al | Bone Anchor and Method of Anchoring a Suture to Bone | 5,037,422 | 8/6/91 |

SUMMARY OF THE INVENTION

1. A Description of the Invention

The instant invention consists of a uniquely designed surgical wedge anchor that differs markedly from any other device of a smaller nature that has been invented previously. The wedge in one embodiment has a barbed top portion, three smooth surfaced sides, two suture holes in the somewhat inclined upper portion of the remaining one of its sides that is not smooth surfaced, two laterally positioned suture holes in its base each one connected to one of the two suture holes in the upper portion of its non smooth surfaced side which, a first centered hole in the middle of the upper portion of the non smooth surfaced side which first centered hole is between and below these two suture holes, a centered hole in its base connected to the first described center hole, an inclination in its base so as to minimize drift of suture thread passing from the two lateral holes in the base to the centered hole in the base and ultimately passing through the first centered hole, and finally, a stop face that angulates outwardly from the plane of the upper portion of the wedge's non-smooth surfaced side in which the abovedescribed holes are found and that serves to separate that side's upper portion from its lower portion inclined in an plane of inclination with direction of inclination similar to the direction of inclination of the plane of inclination of this side's upper portion. The stop face also serves to interface with the inclination in the base of a second wedge when two wedges are utilized for anchoring purposes so as to prevent slippage of one over the other during the end of the anchoring process. The wedge anchor in a second and preferred embodiment reflects all of the features of the first embodiment except that additionally it has a centrally positioned barbed tooth located in an area cut out of the lowest segment of the lower portion of the wedges's non-smooth surfaced side. The wedge anchor in a third embodiment resembles the second embodiment but lacks any paired suture holes in either the upper portion of its non-smooth surfaced side in the inclined portion of the wedge's base. Finally, a fourth embodiment resembles the third embodiment but lacks the tooth found in the third embodiment. A fifth embodiment wherein there is no inclination in the base of the anchor wedge is yet another useful variant. A sixth embodiment is one that resembles any of the abovedescribed embodiments but lacks a stop face. In fact, the abovedescribed preferred embodiment without a stop face is an ideal variant for purposes of serving alone as a wedge anchor.

One or more of the abovedescribed wedges can be utilized to anchor soft tissue to bone by way of suture threading during surgery or soft tissue to soft tissue by way of a suture threading during surgery. Soft tissue connotes either muscle or cartilage or ligaments, for example.

A hole is drilled into bone. Then a hollow insertion tool the base of which is cut at a bias with an outer circumference less than that, of the drilled hole within which there is found a hollow plunger the base of which is cut at a bias with outer circumference less in measure than that of the perimeter of the lower portion of any embodiment but greater in measurement than the inner circumference of the insertion tool or the circumference of suture thread to be utilized, is resorted to for purposes of introducing either one of the preferred embodiments or a plurality of these or one of these in combination with one or more of the other embodiments into the hole to serve as a suture anchor to which soft tissue can be sutured firmly in apposition to such bone. For example, suture thread is passed through the centered holes in the one or more of the latter two embodiments as might be utilized. A knot in the suture thread is tied just below the centered hole in the base of the bottom one of the embodiments to be so utilized. Then the suture material is threaded through the hollow plunger and the plunger together with threaded embodiments are encased within the hollow insertion tool. Then the system is introduced into the hole. Downward pressure is applied to the plunger and this pressure causes the embodiment or embodiments to be so used to be introduced under pressure into the hole in such bone as the insertion tool is simultaneously withdrawn from the hole then, continued downward pressure applied to the plunger coupled with upward pressure on the suture thread causes the wedges to toggle in apposition to one another thus creating an anchor. The barbed tip(s) dig into bone on one side of the hole. The lower tooth (teeth if a plurality of embodiments some of which are third embodiment variants are used) gouge into the other side of the hole by virtue of such applied downward pressure. One toggle wedge, namely, the preferred embodiment also can be used if not so powerful a suture support is desired. Prior to use of this embodiment and insertion via the method described above, suture thread is run down each of the two upper portion suture holes so that a thread bridge runs from one hole to the other. Strands exiting suture holes, one per hole in the base are run up the centered hole in the base and out the first centered hole. These exiting strands are then run under the thread bridge up and away from the wedge. A plurality of wedges can be used to enhance the sturdiness of the suture support depending upon the particular requirements of the surgical procedure being resorted to. If it is desired to suture soft tissue to soft tissue, then, it would not be necessary to preliminarily drill a hole. The system can be initially prepared as noted above and the insertion tool containing within it, the one or more embodiments tied to suture material and plunger can be introduced into the soft tissue by way of merely piercing the tissue. The shape of the embodiments, the manner of suturing, and if a plurality are used for anchoring, then the base inclination and stop face characteristic all cause anchoring by toggling when as previously noted, upward pressure is applied to suture thread along with downward pressure on a plunger.

2. The Object of the Invention

There are numerous and various types of anchor devices in existence today that are designed to facilitate the holding of soft tissue to bone by way of holding surgical sutures sewn into such soft tissue. But, these devices and means such as screws with loops on their crowns, glues and the like are universally amenable to failure over time due to, for example, degradation of bone for breakage at joints within such devices or adhesive defects. Such failure requires readmission of affected patients to surgery and subjugation of such person to the inherent risks and inexorable expense related to the same. Hence, the essential object of the instant invention is to obviate, to the fullest possible extent, such failure.

The instant invention has no relatively delicate joint sites. It functions by way of toggle movement laterally directed and hence once lodged into place simply cannot come loose under the influence of a contemplated physiological load force.

The instant invention is, respectfully submitted, in view of the foregoing, new, indeed revolutionary within its field and unquestionably useful and unique in that it functions in a truly new and unique way as a viable anchor. Moreover, in view of is new and unique type of framework, its dependability from a standpoint of essentially non-susceptibility to breakage in-situ is beyond reproach.

The instant invention is a significant improvement over the suture anchor device which was the subject of the inventor's application entitled "A Suture Anchor" filing date of Oct. 28, 1993 and Ser. No. 08/142,058, since, the relative complexity of and cost of manufacture of the proximal wedge component thereof exceed not insignificantly the same as respects any of the above-mentioned distal wedge embodiments. Moreover, the barbed tip and lower tooth features of the above-mentioned embodiment facilitates even more effective embedding into tissue material especially bone than does the beveled top edge of the distal wedge component of the Suture Anchor especially absent the presence of that device's proximal wedge component.

Finally, the instant device is likewise essentially non-breakable, and, for all of the foregoing reasons, respectfully stated, constitutes a new, useful, and unique advancement in the art relating to devices of this nature.

A DESCRIPTION OF THE DRAWINGS

FIG. 8 is a plan view of the non-smooth surfaced side of the second embodiment of the instant invention.

FIG. 9 is a plan view of the top portion of the second embodiment of the instant invention.

FIG. 10 is a plan view of the smooth front side of the second embodiment of the instant invention.

FIG. 11 is a plan view of the smooth side of the second embodiment of the instant invention opposite the side of the same shown in FIG. 8.

FIG. 12 is a longitudinal cross sectional view of the second embodiment of the instant invention.

FIG. 13 is a plan view of the base of the second embodiment of the instant invention.

FIG. 14 is a perspective view of the second embodiment of the instant invention.

FIG. 22 is a perspective view of an insertion device and plunger device located within the insertion device.

FIG. 23 is a cross-sectional view of an insertion device and plunger device located within the insertion device.

FIG. 24 is a cross-sectional view of the third and fourth embodiments of the instant invention held by a piece of suture thread.

FIG. 25 is a plan view of what is seen in FIG. 24 in apposition to a plunger device and in apposition to an insertion device shown in cross-sectional view.

FIG. 26 is a plan view of a third and fourth embodiment of the instant invention held by suture thread in close apposition to a plunger device show cross-sectionally all within the lumen of an insertion device shown in cross-sectional view.

FIG. 36 shows in plan view the manner in which suture thread can be threaded through the holes of the instant invention's second embodiment in contemplation of its being used alone as a suture anchoring device.

FIG. 37 shows suture material threaded as seen in FIG. 36 but in top plan view.

FIG. 38 shows suture material threaded as seen in FIG. 36 but in front plan view.

FIG. 39 shows in plan view, suture material threaded through suture holes in the inclined base of the instant invention's second embodiment.

FIG. 40 is a bottom plan view of what, is seen in FIG. 39.

FIG. 41 is a perspective view showing the manner in which suture thread can be threaded through the holes of the instant invention's second embodiment in contemplation of its being used alone as a suture anchoring device.

A DESCRIPTION OF THE PREFERRED EMBODIMENT

Figure 42:
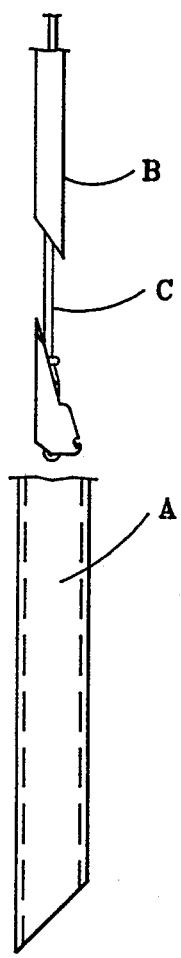
FIG. 42 shows in plan view, a second embodiment of the instant invention about to be inserted into the lumen of an insertion device shown in cross-sectional view.
Figure 43:
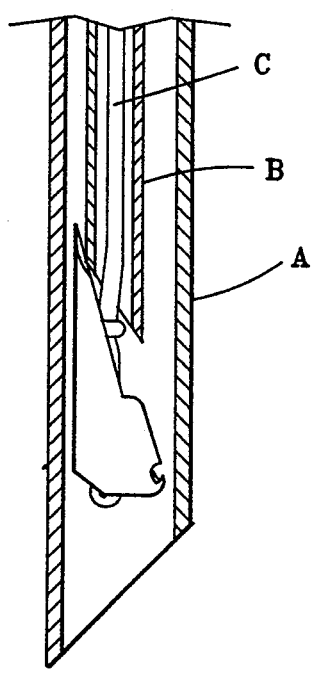
FIG. 43 shows in plan view a second embodiment of the instant invention in apposition to a plunger device shown in cross-sectional view within the linen of an insertion device shown in cross-sectional view.
Figure 44:
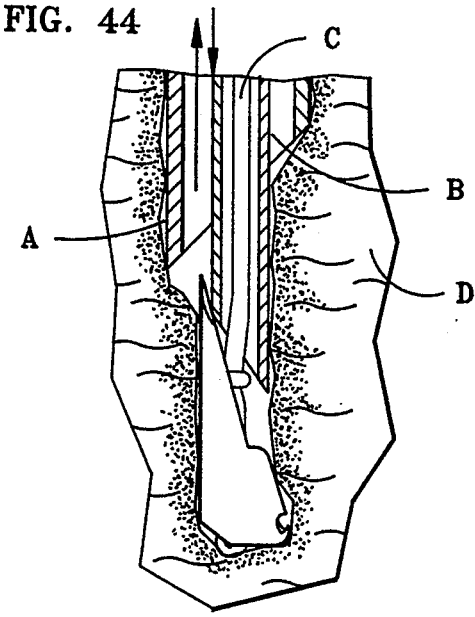
FIG. 44 shows downward pressure on a plunger device shown in cross-sectional view concomitant with withdrawal of an insertion device shown in cross-sectional view within a piece of soft tissue and commencement of the toggling of the second embodiment of the instant invention.
Figure 45:
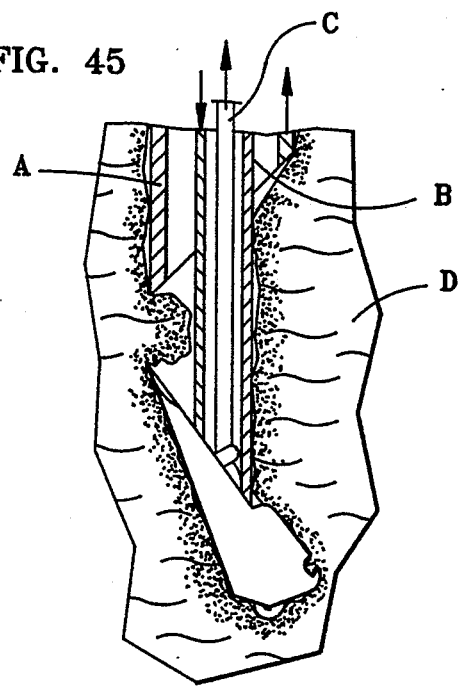
FIG. 45 shows continued downward pressure on a plunger device shown in cross-sectional view concomitant with upward pressure on suture material tied to a second embodiment of the instant invention in furtherance of the toggling of the second embodiment of the instant invention.
Figure 46:
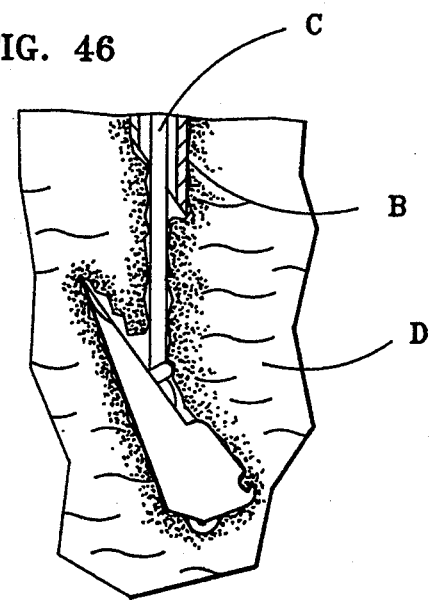
FIG. 46 shows the second embodiment of the instant invention subsequent to completion of the process depicted in FIG. 45 wherein the second embodiment is ready to serve as an anchor within soft tissue.

FIG. 36 is a plan view of the side of the preferred embodiment of the instant device that is characterized by the presence of the device's two suture entry holes, hole 1 and hole 2, its suture exit hole 3b, its barbed tip 5 located in its top portion and its centrally located lower tooth 6 within a rounded out notch 7 in the lowest part of the lower portion of this side, to wit, of the device's only side that has holes in it. Barbed tip 5 located in the device's top portion serves to pierce into tissue on one side of a pierced insertion hole opposite to the side of the hole bitten into by lower tooth 6 as seen in FIG. 46 after the embodiment is threaded as shown with suture material C and suture material C is threaded through a hollow plunger B, an example of which is seen in FIG. 42 and then inserted along with plunger B into the lumen of insertion device A as shown in FIG. 43, and then after soft tissue D is pierced with insertion device A and then downward pressure is applied to plunger B as insertion device A is withdrawn as seen in FIG. 44 followed by continued downward pressure on plunger B and upward pressure on suture material C as shown in FIG. 45. Once anchoring in soft tissue D is accomplished as shown in FIG. 46, then soft tissue D is amenable to being sutured to other soft tissue in close proximity thereto with virtually no fear that the sutured tissues will later come apart due to failure of suturing to hold the tissues together. FIG. 37, FIG. 38, FIG. 39 and FIG. 40 show how suture material C is threaded through suture entry holes 1 and 2 and down through the body of the embodiment and out through suture exit holes 1b and 2b respectively in the inclined portion of the base of the embodiment, then up through suture entry hole 3 also located in the base of the embodiment and then out through suture exit hole 3b located in the upper portion of the side of this embodiment characterized by the presence of suture entry holes 1 and 2 with hole 3b located between and below holes 1 and 2. The nexus 2a between holes 2 and 2b and the nexus 3a between holes 3 and 3b are seen in FIG. 12. Rotation of FIG. 12 through an angle of 180 degrees would disclose a separate nexus between holes 1 and 1b equivalent in dimension to that of nexus 2a. It has been noted to be the case that it is singularly important to run the ends of suture material C exiting hole 3b under the arch of suture material C formed when suture material C is initially threaded through holes 1 and 2 in order to maximize the toggling effect on the embodiment as suture thread C is pulled upwards with downward pressure applied to plunger B as seen in FIG. 45. FIG. 41 shows in perspective view what is depicted in FIG. 36.

Figure 1:
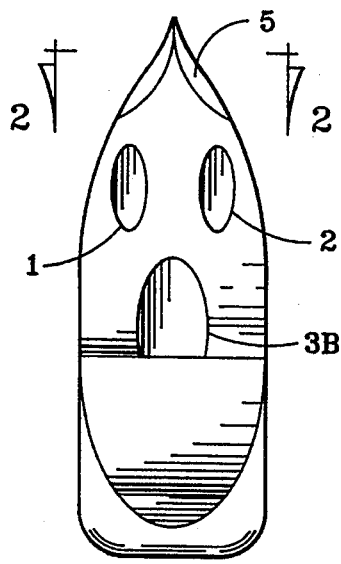
FIG. 1 is a plan view of the non-smooth surfaced side of the first embodiment of the instant invention.
Figure 2:
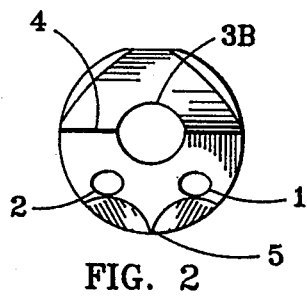
FIG. 2 is a plan view of the top portion of the first embodiment of the instant invention.
Figure 3:
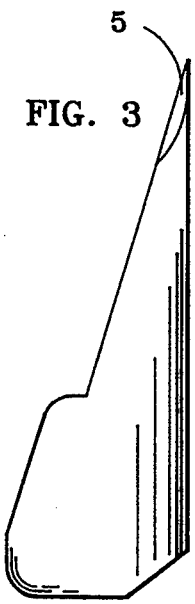
FIG. 3 is a plan view of the smooth front side of the first embodiment of the instant invention.
Figure 4:
FIG. 4 is a plan view of the smooth side of the first embodiment of the instant invention opposite the side of the same shown in FIG. 1.
Figure 5:
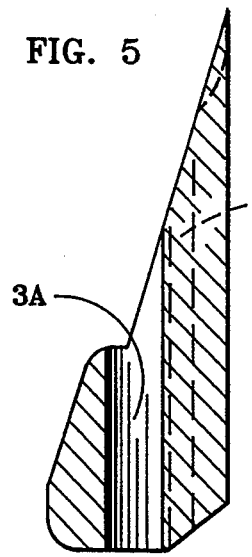
FIG. 5 is a longitudinal cross-sectional view of the first embodiment of the instant invention.
Figure 6:
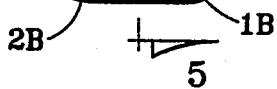
FIG. 6 is a plan view of the base of the First embodiment of the instant invention.
Figure 7:
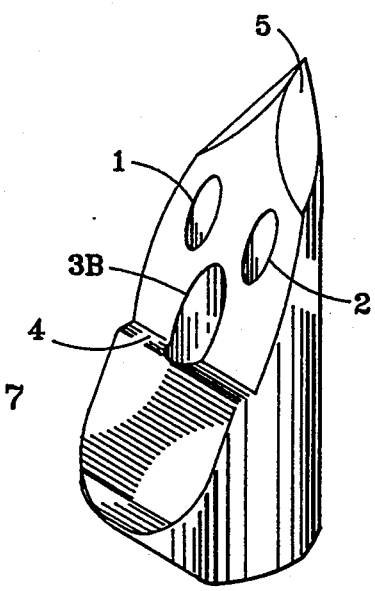
FIG. 7 is a perspective view of the first embodiment of the instant invention.
Figure 15:
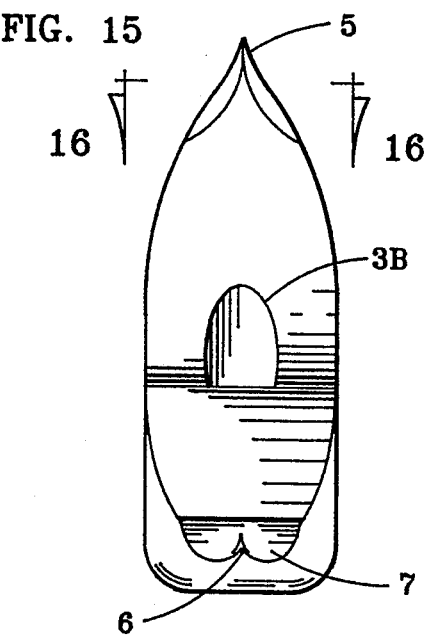
FIG. 15 is a plan view of the non-smooth surfaced side of the third embodiment of the instant invention.
Figure 16:
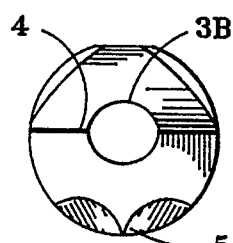
FIG. 16 is a plan view of the top portion of the third embodiment of the instant invention.
Figure 17:
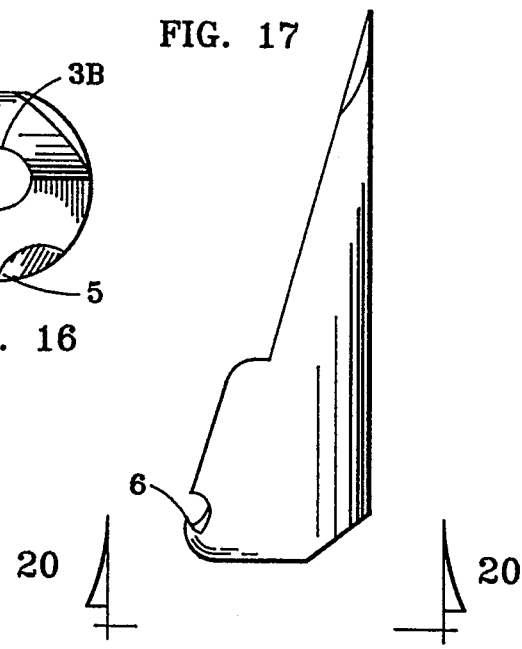
FIG. 17 is a plan view of the smooth front side of the third embodiment of the instant invention.
Figure 18:
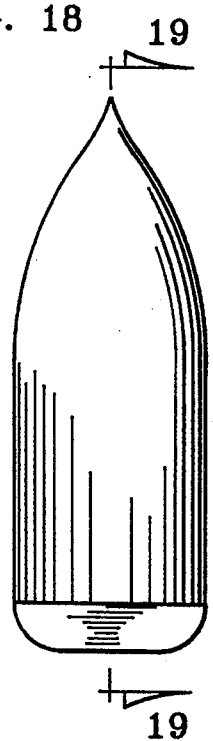
FIG. 18 is a plan view of the smooth side of the third embodiment of the instant invention opposite the side of the same shown in FIG. 15.
Figure 19:
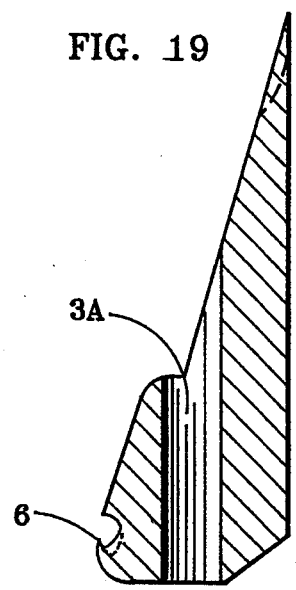
FIG. 19 is a longitudinal cross-sectional view of the third embodiment of the instant invention.
Figure 20:
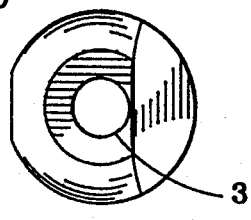
FIG. 20 is a plan view of the base of the third embodiment of the instant invention.
Figure 21:
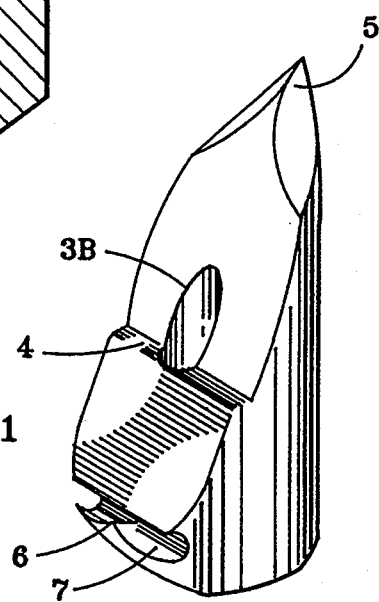
FIG. 21 is a perspective view of the third embodiment of the instant invention.
Figure 27:
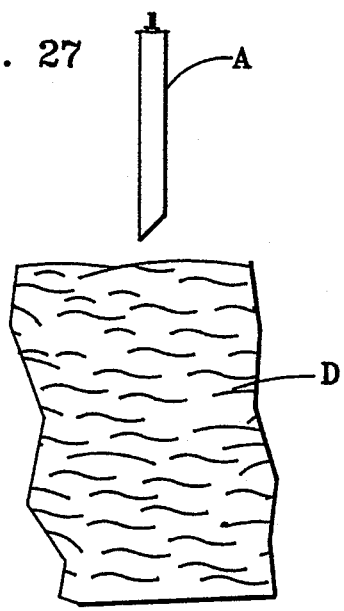
FIG. 27 shows an insertion device prior to its piercing a piece of soft tissue. There is also shown, suture material through the top of a plunger device shown within the insertion device.
Figure 28:
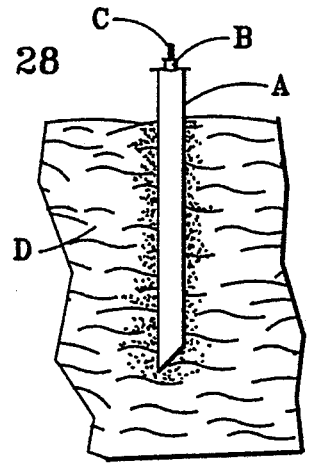
FIG. 28 shows an insertion device having pierced a piece of soft tissue. There is also shown, suture material through the top of a plunger device shown within the insertion device.
Figure 29:
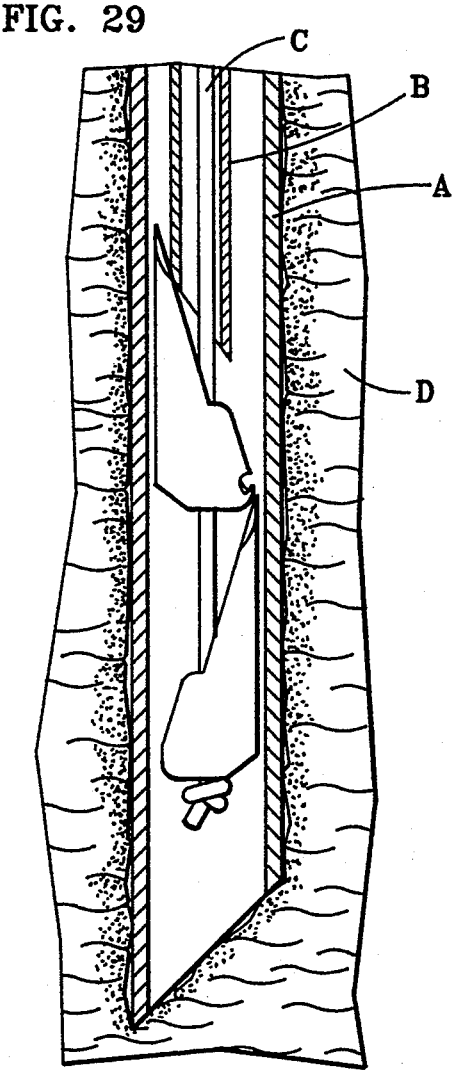
FIG. 29 is an enlarged plan view of the third and fourth embodiments of the instant invention held by suture thread in apposition to a plunger device in cross-sectional view within the lumen of an insertion device shown in cross-sectional view embedded within a piece of soft tissue.
Figure 30:
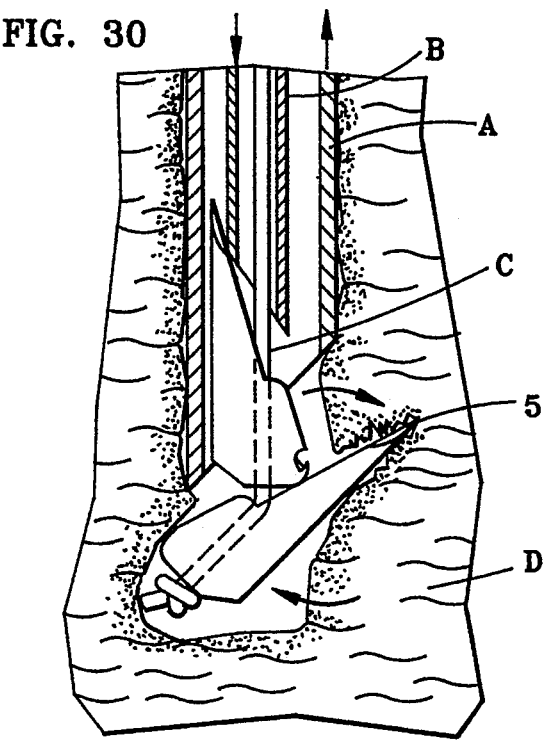
FIG. 30 is an isolated enlarged view of the lower portion of an insertion device shown in cross-sectional view embedded in soft tissue material within which are found the plunger device shown in cross-sectional view and part of the third embodiment of the instant invention when downward pressure is applied to the plunger device as the insertion device is being withdrawn.
Figure 31:
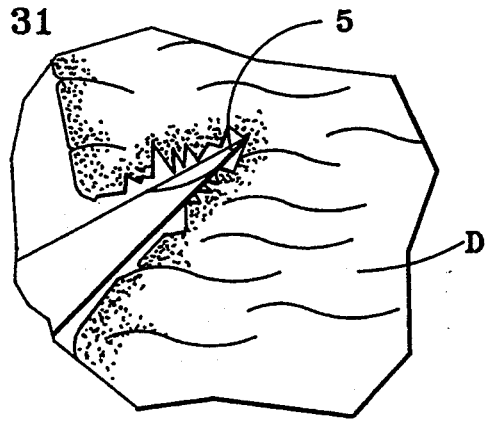
FIG. 31 is an isolated view of the barbed top portion of the instant invention biting into soft tissue when downward pressure is applied to the plunger device as the insertion device is being withdrawn.
Figure 32:
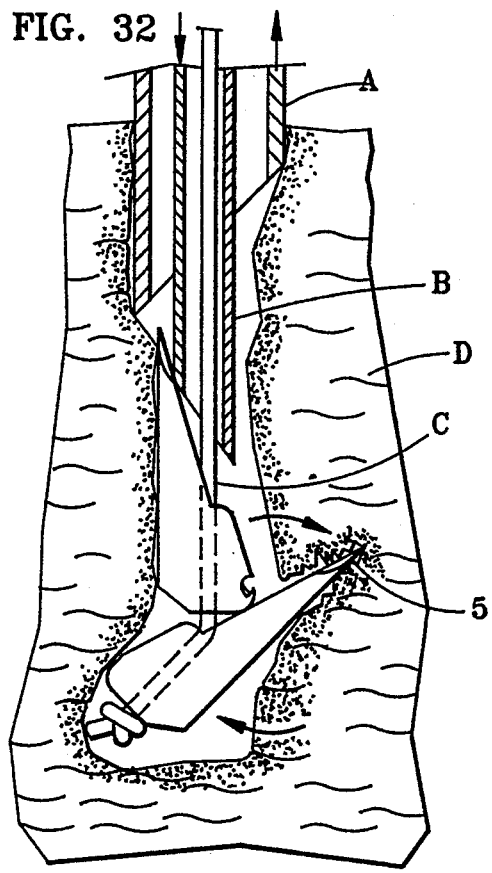
FIG. 32 shows the action of the embodiments of the invention in respect biting into tissue as the process referenced in FIG. 31 is continued.
Figure 33:
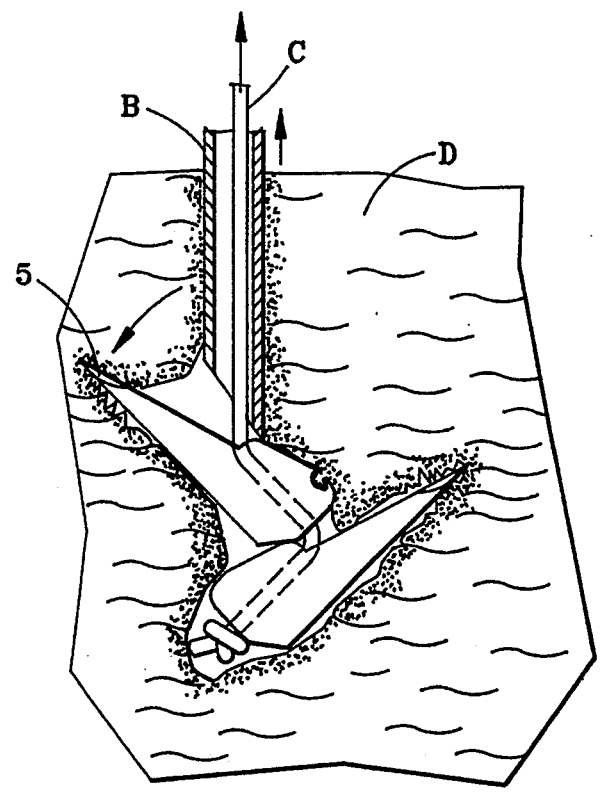
FIG. 33 shows the further biting into soft tissue by the embodiments of the instant invention as upward pulling pressure is applied to the suture material affixed thereto.
Figure 34:
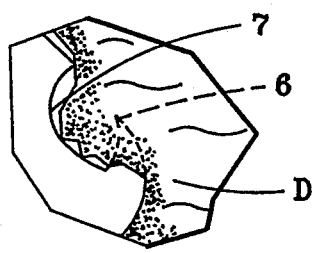
FIG. 34 is a close-up isolated view of the bite into soft tissue by the centrally positioned barbed tooth of the third embodiment of the instant invention.
Figure 35:
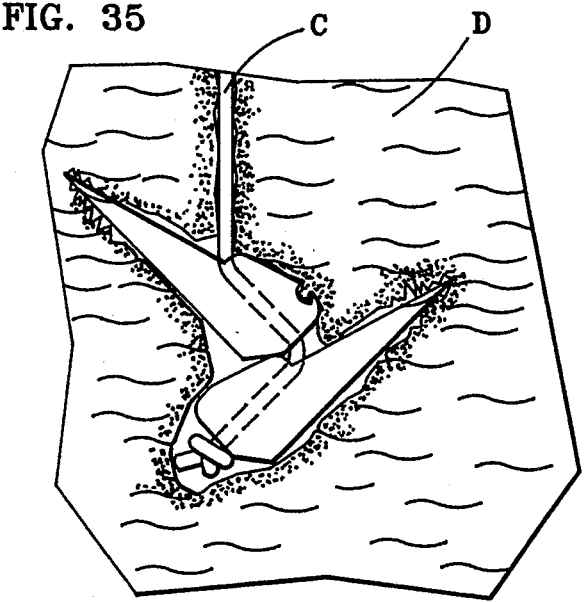
FIG. 35 is an isolated view of the resultant anchoring within soft tissue of suture material by virtue of completion of the process described in FIG. 34 above.

FIGS. 8–14 inclusive excepting FIG. 12 depict the various views of the preferred embodiment of the instant invention as are seen in FIGS. 36-41 inclusive but without the suture material C threaded through the various holes present within the embodiment. FIGS. 1-7 inclusive depict various views of another embodiment of the instant invention. This latter embodiment lacks the centrally located lower tooth 6 and notch 7 of the preferred embodiment. This other latter embodiment can be utilized in conjunction with the preferred embodiment, for example, for embedding in bone when one might be seeking to hold a greater tissue load than an anchor made up of only one wedge embodiment, namely, the preferred embodiment alone. As might be expected, two exemplars of the preferred embodiment could be utilized for purposes of constructing such a relatively stronger anchor. This latter embodiment does not have the overall holding capacity of the preferred embodiment, but, it is somewhat less expensive to manufacture due to its relative simplicity of design. FIGS. 15-21 inclusive depict yet a third embodiment of the instant invention. This third embodiment is simpler in design than the former two and is less expensive to manufacture. An even simpler embodiment, namely, the lower of the two embodiments utilized for anchoring purposes as seen in FIGS. 25 and 26 resembles the third embodiment but lacks the centrally located lower tooth 6 and notch 7 of the third embodiment. These latter two embodiments lack paired lateral suture holes 1 and 2 and paired suture holes 1b and 2b on the bases of these embodiments and correspondingly lack as well nexus' between holes 1 and 1b, namely nexus 1a and between holes 2 and 2b, namely nexus 2a. FIGS. 22-26 inclusive demonstrate how these latter two embodiments would be tied together with suture material C, placed below plunger B through which suture material C would have been threaded and placed in-toto within the lumen of insertion device A. Device A is then inserted into tissue D as per FIGS. 27, 28 and 29. Withdrawal of the device A coupled with downward pressure on plunger B constitutes commencent of the process that ultimately causes the wedge system to be toggled wedged into tissue D. Barbed tip 5 pierces into tissue D as seen in FIGS. 30 and 31. FIG. 32 illustrates the commencement of such toggle anchoring with withdrawal of device A coupled with downward pressure on plunger B. FIG. 33 shows completion of toggle anchoring with upward pulling pressure on suture thread C as plunger B is concomitantly withdrawn. FIG. 34 shows in isolated view, tooth 6 having bitten into tissue D on the wall of tissue D opposite to the wall pierced by barbed tip 5. FIG. 35 shows a fully constructed suture anchor with the inclined base of one wedge in apposition to the stop face 4 of a second wedge. The preferred embodiment threaded as shown previously could have been utilized in lieu of the fourth embodiment as shown in FIGS. 27 through 35, and for that matter so could have the embodiment shown in FIGS. 1-7 inclusive above if threaded as shown in FIGS. 36 and 41, but simplicity of design and diminished cost of manufacture would be factors that would, no doubt, prompt use of the third and fourth embodiments for purposes of accomplishing sturdy toggle anchoring in tissue in excess of the sturdiness to be appreciated from use of the preferred embodiment alone as per the protocol evidenced with resort to FIGS. 42-46 inclusive. The preferred embodiment and its less expensive counterpart, to wit, the embodiment shown in FIGS. 1-7 could however be used in tandem to accomplish extra sturdy anchoring in bone.

What is claimed is:

1. A toggle wedge for anchoring suture thread in bone or soft tissue, comprising:
  a. a front side;
  b. a first lateral side connected to said front side;
  c. a back side connected to said first lateral side;
  d. a second lateral side connected to said front side and said back side;
  e. a base made up of a fiat portion and an upwardly inclined portion which said upwardly inclined portion has a bottom boundary line that abounds said fiat portion and an upper boundary line that abounds and is connected to the bottom boundary line of said first lateral side and which said base is connected as well to said front side, said second lateral side, said first lateral side, and said back side;.
  f. a top portion that tapers to a sharp tip;
  g. a first hole positioned in the upper half of said second lateral side which said second lateral side is opposite in position to that of said first lateral side;
  h. a second hole positioned in said upper half of said second lateral side;
  i. a third hole positioned in said upper half of said second lateral side;
  j. a fourth hole positioned in the said fiat portion of said base;
  k. a canal leading from said third hole through the body of said toggle wedge to said fourth hole;
  l. the said bottom boundary line of which said upwardly inclined portion abuts the circumference of said fourth hole and extends from the bottom of said toggle wedge's said front side to the bottom of said toggle wedge's said back side opposite in position to said front side;
  m. a fifth hole in said upwardly inclined portion of said base of said toggle wedge;
  n. a sixth hole in said upwardly inclined portion of said base of said toggle wedge;
  o. two canals coursing through the said body of said toggle wedge in directions parallel to one another leading one each respectively from said fifth hole and said sixth hole to said first hole and said second hole respectively.

2. A toggle wedge for anchoring suture thread in bone or soft tissue, comprising.
  a. a front side;
  b. a first lateral side connected to said front side;
  c. a back side connected to said first lateral side;
  d. a second lateral side connected to said front side and said back side;
  e. a base made up of a flat portion and an upwardly inclined portion which said upwardly inclined portion has a bottom boundary line that abounds said fiat portion and an upper boundary line that abounds and is connected to the bottom boundary line of said first lateral side and which said base is connected as well to said front side, said second lateral side, said first lateral side, and said back side;
  f. a top portion that tapers to a sharp tip;
  g. a first hole positioned in the upper haw of said second lateral side which said second lateral side is opposite in position to that of said first lateral side;
  h. a second hole positioned in said upper half of said second lateral side;
  i. a third hole positioned in said upper half of said second lateral side;
  j. a fourth hole positioned in said fiat portion of said base;

k. a canal leading from said third hole through the body of said toggle wedge to said fourth hole;

l. the said bottom boundary line of which said upwardly inclined portion abuts the circumference of said fourth hole and extends from the bottom of said toggle wedge's said front side to the bottom of said toggle wedge's said back side opposite in position to m. a fifth hole in said upwardly inclined portion of said base of said toggle wedge;

n. a sixth hole in said upwardly inclined portion of said base of said toggle wedge;

o. two canals coursing through the said body of said toggle wedge in directions parallel to one another leading one each respectively from said fifth hole and said sixth hole to said first hole and said second hole respectively.

p. a rounded notch cut out of nearly the lowest part of the lower half of said second lateral side and extending horizontally from said front side to said back side and tapering symmetrically to a sharp tip in the midline of the lowest portion of said notch.

3. A toggle wedge for anchoring suture thread in bone or soft tissue, comprising:
a. a front side;
b. a first lateral side connected to said front side;
c. a back side connected to said first lateral side;
d. a second lateral side connected to said front side and said back side;
e. a base made up of a fiat portion and an upwardly inclined portion which said upwardly inclined portion has a bottom boundary line that abounds said fiat portion and an upper boundary line that abounds and is connected to the bottom boundary line of said first lateral side and which said base is connected as well to said front side, said second lateral side, said first lateral side, and said back side;
f. a top portion that tapers to a sharp tip;
g. a first hole centrally positioned in the upper half of said second lateral side;
h. a second hole located in said base of said toggle wedge;
i. a canal leading from said first hole through the body of said toggle wedge to said second hole.

4. A toggle wedge for anchoring suture thread in bone or soft tissue, comprising:
a. a front side;
b. a first lateral side connected to said front side;
c. a back side connected to said first lateral side;
d. a second lateral side connected to said front side and said back side;
e. a base made up of a fiat portion and an upwardly inclined portion which said upwardly inclined portion has a bottom boundary line that abounds said fiat portion and an upper boundary line that abounds and is connected to the bottom boundary line of said first lateral side and which said base is connected as well to said front side, said second lateral side, said first lateral side, and said back side;
f. a top portion that tapers to a sharp tip;
g. a first hole centrally positioned in the upper half of said second lateral side;
h. a second hole located in said base of said toggle wedge;
i. a canal leading from said first hole through the body of said toggle wedge to said second hole;
j. a rounded notch cut out of nearly the lowest part of the lower half of said second lateral side and extending horizontally from said front side to said back side and tapering symmetrically to a sharp tip in the midline of the lowest portion of said notch.

5. A toggle wedge for anchoring suture thread in bone or soft tissue, comprising:
a. a front side;
b. a first lateral side connected to said front side;
c. a back side connected to said first lateral side;
d. a second lateral side connected to said front side and said back side;
e. a base connected to said front side, said first lateral side, said back side and said second lateral side;
f. a top portion that tapers to a sharp tip;
g. a first hole positioned in the upper haft of said second lateral side which said second lateral side is opposite in position to that of said first lateral side;
h. a second hole positioned in said upper half of said second lateral side;
i. a third hole positioned in said upper half of said second lateral side between said first hole and said second hole;
j. a fourth hole located in said base of said toggle wedge;
k. a canal leading from said third hole through the body of said toggle wedge to said fourth hole;
l. a fifth hole in said base of said toggle wedge;
m. a sixth hole in said base of said toggle wedge;
n. two canals coursing through the body of said toggle wedge in directions parallel to one another leading one each respectively from said fifth hole and said sixth hole to said first hole and said second hole respectively;

6. A toggle wedge for anchoring suture thread in bone or soft tissue, comprising:
a. a front side;
b. a first lateral side connected to said front side;
c. a back side connected to said first lateral side;
d. a second lateral side connected to said front side and said back side;
e. a base connected to said front side, said first lateral side, said back side and said second lateral side;
f. a top portion that tapers to a sharp tip;
g. a first hole positioned in the upper haw of said second lateral side which said second lateral side is opposite in position to that of said first lateral side;
h. a second hole positioned in said upper half of said second lateral side;
i. a third hole positioned in the upper half of said second lateral side between said first hole and said second hole;
j. a fourth hole located in said base of said toggle wedge;
k. a canal leading from said third hole through the body of said toggle wedges to said fourth hole;
l. a fifth hole in said base of said toggle wedge;
m. a sixth hole in said base of said toggle wedge;
n. two canals coursing through the body of said toggle wedge in directions parallel to one another leading one each respectively from said fifth hole and said sixth hole to said first hole and said second hole respectively;
o. a rounded notch cut out of nearly the lowest part of the lower half of said second lateral side and extending horizontally from said front side to said back side and tapering symmetrically to a sharp tip in the midline of the lowest portion of said notch.

* * * * *